(12) United States Patent
Diec et al.

(10) Patent No.: US 6,667,044 B1
(45) Date of Patent: Dec. 23, 2003

(54) COSMETIC OR DERMATOLOGICAL GELS BASED ON MICROEMULSIONS

(75) Inventors: Khiet Hien Diec, Hamburg (DE); Wolfgang Meier, Basel (CH); Jörg Schreiber, Hamburg (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/269,676

(22) PCT Filed: Oct. 2, 1997

(86) PCT No.: PCT/EP97/05418

§ 371 (c)(1),
(2), (4) Date: Jun. 18, 1999

(87) PCT Pub. No.: WO98/15254

PCT Pub. Date: Apr. 16, 1998

(30) Foreign Application Priority Data

Oct. 4, 1996 (DE) .......................................... 196 40 877
Oct. 12, 1996 (DE) .......................................... 196 42 090

(51) Int. Cl.[7] .......................... A61K 7/00; A61K 31/74; A61K 9/14
(52) U.S. Cl. .................... 424/401; 424/78.03; 424/484; 424/486; 514/937; 514/938; 514/941; 514/943; 514/944
(58) Field of Search .................................. 424/401, 484, 424/486, 78.03; 514/944, 941, 943, 937, 938

(56) References Cited

U.S. PATENT DOCUMENTS 5,474,776 A   12/1995   Koyanagi et al. ............ 424/401

FOREIGN PATENT DOCUMENTS

| DE | 281 960   | 8/1990 |
| DE | 44 11 557 | 10/1995 |
| EP | 0 514 934 | 11/1992 |
| EP | 0 529 883 | 3/1993 |
| EP | 0 815 837 | 1/1998 |
| FR | 2 693 733 | 1/1994 |
| GB | 2 242 358 | 10/1991 |
| WO | 96 28132  | 9/1996 |

Primary Examiner—Shelley A. Dodson
(74) Attorney, Agent, or Firm—Norris McLaughlin & Marcus

(57) ABSTRACT

Microemulsion gels a) based on water in oil type microemulsions, comprising an oil phase which is essentially composed of not easily volatile components, an aqueous phase containing one or more polyethoxylated W/O emulsifiers and/or one or more polypropoxylated W/O emulsifiers and/or one or more polyethoxylated and polypropoxylated W/O emulsifiers and/or one or more monoesters, diesters, polyesters of polyols as W/O emulsifiers and/or one or more monoethers, diethers, polyethers of polyols as W/O emulsifiers and/or one or more dimethicone copolyols as W/O emulsifiers and/or one or more fatty alcohols or fatty acids as W/O emulsifiers and/or one or more sorbitan esters as W/O emulsifiers and/or one or more methyl glucose esters as W/O emulsifiers, and also comprising if desired one or more O/W emulsifiers, obtained in such a way that a mixture of basic components comprising an aqueous phase, an oil phase, one or more inventive emulsifiers is produced, being the HLB value of the emulsifier or emulsifier combination located between 2 and 14.

14 Claims, 1 Drawing Sheet

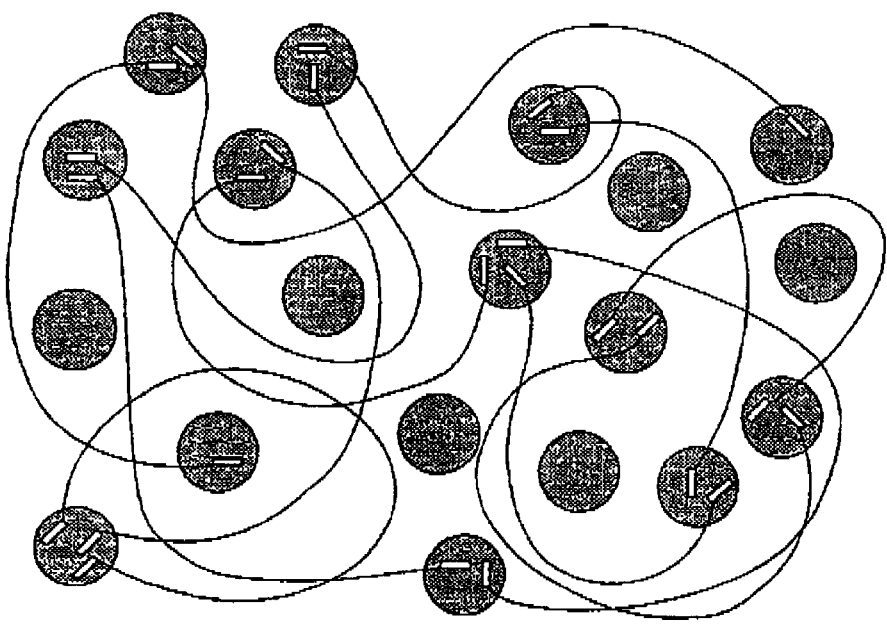

COSMETIC OR DERMATOLOGICAL GELS BASED ON MICROEMULSIONS

This application is a 371 application of PCT/EP 97/05418 (WO 98/15254), which was filed on Oct. 2, 1997.

The present invention relates to cosmetic or dermatological gels based on microemulsions, in particular such gels for cosmetic and dermatological formulations. As a particular embodiment, the present invention relates to cosmetic or dermatological gels based on microemulsions of the water-in-oil type, processes for their preparation and their use for cosmetic and medical purposes.

Cosmetic skin care is primarily to be understood as meaning that the natural function of the skin as a barrier against environmental influences (for example dirt, chemicals and microorganisms) and against the loss of endogenous substances (for example water, natural fats and electrolytes) is intensified or re-established.

If this function is impaired, increased absorption of toxic or allergenic substances or attack by microorganisms and as a consequence toxic or allergic skin reactions may occur.

The aim of skin care is furthermore to compensate the loss of fats and water from the skin caused by daily washing. This is important particularly if the natural capacity for regeneration is not adequate. Skin-care products should furthermore protect against environmental influences, in particular against the sun and wind, and delay ageing of the skin.

Medical topical compositions as a rule comprise one or more medicaments in an active concentration. For simplicity, reference is made to the legal provisions of the Federal Republic of Germany (for example cosmetics legislation, legislation on foodstuffs and medicaments) for a clear distinction between cosmetic and medical use and corresponding products.

Gels are customary cosmetic and dermatological formulation forms which have become more and more widespread particularly in recent times.

In the technical sense, gels are understood as meaning: relatively dimensionally stable, easily deformable disperse systems of at least two components, which as a rule comprise a—usually solid—colloidally divided substance of long-chain molecular grouping (for example gelatin, silicic acid or polysaccharides) as the matrix-forming phase and a liquid dispersant (for example water). The colloidally divided substance is often called a thickener or gelling agent. It forms a three-dimensional network in the dispersant, it being possible for individual particles present in colloidal form to be linked to one another more or less firmly via electro-static interaction. The dispersant, which surrounds the network, is distinguished by electrostatic affinity for the gelling agent, i.e. a predominantly polar (in particular: hydrophilic) gelling agent preferably gels a polar dispersant (in particular: water), whereas a predominantly non-polar gelling agent preferably gels non-polar dispersants.

Strong electrostatic interactions, which are realized, for example, in hydrogen bridge bonds between the gelling agent and dispersant, but also between dispersant molecules with one another, can lead to a high degree of crosslinking of the dispersant as well. Hydro-gels can comprise water to the extent of almost 100% (alongside, for example, about 0.2–1.0% of a gelling agent), and at the same time have an entirely solid consistency. The water content is present here in ice-like structural elements, so that gels entirely justify the origin of their name [from lat. "gelatum"="frozen" by the alchemistic term "gelatina" (16th century) for the modern term "gelatin"].

Lipogels and oleogels (of waxes, fats and fatty oils) as well as carbogels (from paraffin or petrolatum) are furthermore also customary in cosmetic and pharma-ceutical galenics. In practice, a distinction is made between oleogels, which are in practically anhydrous form, hydrogels, which are practically fat-free, and oil/water gels which are ultimately based on O/W or W/O emulsions but in which features of a gel structure are additionally also realized. Gels are usually transparent. In cosmetic and pharmaceutical galenics, gels are as a general rule distinguished by a semi-solid, often free-flowing consistency.

In simple emulsions, in the one phase, finely dispersed droplets of the second phase (water droplets in W/O or lipid vesicles in O/W emulsions) enclosed by an emulsifier shell are present. The droplet diameters of the usual emulsions are in the range from about 1 $\mu$m to about 50 $\mu$m. Without further colouring additives, such "macroemulsions" are milky white in colour and opaque. Finer "macroemulsions", the droplet diameters of which are in the range from about $10^{-1}$ $\mu$m to about 1 $\mu$m, again without colouring additives, are bluish-white in colour and non-transparent.

It is the property of micellar and molecular solutions having particle diameters of less than about $10^{-2}$ $\mu$m to appear clear and transparent.

The droplet diameter of transparent or translucent microemulsions, on the other hand, is in the range from about $10^{-2}$ $\mu$m to about $10^{-1}$ $\mu$m. Such microemulsions usually have a low viscosity.

So-called surfactant gels are furthermore customary formulations of the prior art. These are ,understood as being systems which, in addition to water, have a high concentration of emulsifiers, typically more than about 25% by weight, based on the total composition. If oil components are solubilized in these surfactant gels, which is their technical name, microemulsion gels, which are also called "ringing gels" are obtained. Cosmetically more elegant microemulsion gels can be obtained by addition of nonionic emulsifiers, for example alkyl polyglycosides. Here also, the high content of emulsifiers is a disadvantage.

An advantage of microemulsion gels is that active compounds can be present in finely disperse form in the disperse phase. Another advantage is that, because of their low viscosity, they can be sprayed. When micro-emulsions are used as cosmetics, corresponding products are distinguished by a high cosmetic elegance.

It is known per se to link the droplets of a low-viscosity, in particular thinly liquid microemulsion with crosslinking substances with one another, in order to obtain the three-dimensional network of a gel in this manner.

Chain-like, hydrophilic molecules which contain a hydrophobic radical on each of the two chain ends are described in Nachr. Chem. Techn. Lab. 43 (1995) No. 1, page 9 et seq for crosslinking microemulsion droplets. Those hydrophobic radicals are immersed in the micro-emulsion droplets, the hydrophilic chain regions being in the continuous aqueous phase. In the strict sense, it is certainly not necessary for the hydrophobic radicals to be "immersed". In individual cases, it can also be entirely sufficient if the hydrophobic radicals come into contact with the surface of the microemulsion droplets by hydrophobic interaction and remain stuck to these more or less firmly.

Crosslinkers which are mentioned in the above reference are polyoxyethylene glycols with oleyl groups as hydrophobic end groups.

A disadvantage of microemulsions, and therefore also of the microemulsion gels of the prior art, is that a high content of one or more emulsifiers must always be employed, since the low droplet size results in a high interface between the phases, which as a rule must be stabilized by emulsifiers.

The use of the customary cosmetic emulsifiers is indeed acceptable per se. Nevertheless, emulsifiers, like any chemical substance in the end, can cause allergic reactions or reactions based on hypersensitivity of the user in an individual case.

It is thus known that particular photodermatoses are induced by certain emulsifiers, and also by various fats, and simultaneously exposure to sunlight. Such photodermatoses are also called "Majorca acne". An object of the present invention was therefore to develop sun-screen products.

As particular embodiments, the present invention thus relates to cosmetic and dermatological light protection formulations, in particular skin-care cosmetic and dermatological light protection formulations.

The damaging effect of the ultraviolet part of solar radiation on the skin is generally known. While rays having a wavelength of less than 290 nm (the so-called UVC range) are absorbed by the ozone layer in the Earth's atmosphere, rays in the range between 290 nm and 320 nm, the so-called UVB range, cause erythema, simple sunburn or even actual burns of greater or lesser severity.

The narrower range around 308 nm is seen as the erythema activity maximum of sunlight.

Numerous compounds are known for protection against UVB radiation, these usually being derivatives of 3-benzylidenecamphor, of 4-aminobenzoic acid, of cinnamic acid, of salicylic acid, of benzophenone and also of 2-phenylbenzimidazole.

For the range between about 320 nm and about 400 nm, the so-called UVA range, it is also important to have available filter substances, since the rays thereof can also cause damage. It has thus been proved that UVA radiation leads to damage to the elastic and collagenic fibres of connective tissue, which makes the skin age prematurely, and that it has to be regarded as a cause of numerous phototoxic and photoallergic reactions. The damaging effect of UVB radiation can be intensified by UVA radiation.

However, UV radiation can also lead to photo-chemical reactions, the photochemical reaction products then intervening in the skin metabolism.

To prevent these reactions, antioxidants and/or agents which trap free radicals can additionally be incorporated into the cosmetic or dermatological formulations.

Most inorganic pigments, which are known to be used in cosmetics for protecting the skin against UV rays, are UV absorbers or UV reflectors. These pigments are oxides of titanium, zinc, iron, zirconium, silicon, manganese, aluminium and cerium, and mixtures thereof, as well as modifications.

Microemulsion gels are also suitable for other cosmetic dermatological uses, for example deodorants, so that in a particular embodiment, the present invention relates to microemulsion gels as a base for cosmetic deodorants.

Cosmetic deodorants serve to eliminate body odour, which develops when fresh perspiration, which is odourless per se, is decomposed by microorganisms. The customary cosmetic deodorants are based on various action principles.

In so-called antiperspirants, the formation of perspiration can be reduced by astringents—chiefly aluminium salts, such as aluminium hydroxy chloride (hydrated aluminium chloride).

By using antimicrobial substances in cosmetic deodorants, the bacterial flora on the skin can be reduced. In the ideal case, only the odour-causing microorganisms should be effectively reduced here. The flow of perspiration itself is not influenced as a result, and in the ideal case only the microbial decomposition of the perspiration is temporarily stopped.

Combination of astringents with antimicrobially active substances in one and the same composition is also customary.

Deodorants should meet the following conditions:
1) They should cause reliable deodorization.
2) The natural biological processes of the skin must not be impaired by the deodorants.
3) The deodorants must be harmless in the event of an overdose or if used other than as specified.
4) They should not become concentrated on the skin after repeated use.
5) They should be easy to incorporate into customary cosmetic formulations.

Both liquid deodorants, for example aerosol sprays, roll-ons and the like, and solid formulations, for example deodorant sticks, powders, powder sprays, intimate cleansing compositions and the like, are known and customary.

The use of microemulsions as a base for formulations having a deodorizing or antiperspirant action is also known. Their relatively high content of emulsifiers with the disadvantages described has to date been a poor state of affairs which was to be remedied.

Another object of the present invention was thus to develop formulations which are suitable as a base for cosmetic deodorants or antiperspirants and do not have the disadvantages of the prior art.

It was furthermore an object of the invention to develop cosmetic bases for cosmetic deodorants which are distinguished by a good skin tolerability.

It was furthermore an object of the present invention to provide products based on microemulsion gels with the broadest possible diversity of uses. For example, bases for formulation forms such as cleansing emulsions, face- and body-care formulations, and also distinctly medical/pharmaceutical presentation forms, for example formulations against acne and other skin manifestations, were to be provided.

In a particular embodiment, the invention therefore relates to microemulsions for moistening the skin or for stabilizing sensitive active compounds such as, for example, vitamin C, or enzymes.

Waterproof eye make-up, for example mascara, can be removed satisfactorily with water-based make-up removers only with special surfactants. However, these surfactants often have only a limited physiological tolerability. When such substances come into contact with the mucous membrane, in particular the mucous membrane of the eye, these substances lead to irritation, which manifests itself, for example, in a reddening of the eyes. Reactions of this type are typical, of surfactant-containing products.

An object of the present invention is consequently to provide a remedy for such problems.

In another embodiment, the present invention relates to hair cosmetics formulations. In particular, the present invention relates to hair cosmetics formulations for care of the hair and the scalp. In a preferred embodiment, the present invention relates to formulations which serve to strengthen the individual hairs and/or to impart hold and fullness to the hairstyle overall.

Roughly speaking, human hair can be divided into the living part, the hair root, and the dead part, the hair shaft. The hair shaft in turn comprises the medulla, which nevertheless through evolution has become insignificant for modern man and has receded, and in the case of thin hair is often absent entirely, and furthermore the cortex which surrounds the medulla and the cuticula which encloses the entirety of the medulla and cortex.

The cuticula in particular, but also the keratinous region between the cuticula and cortex, as the outer shell of the hair, are exposed to particular demands due to environmental influences, due to combing and brushing, and also due to hair treatment, in particular colouring of the hair and deforming of the hair, for example permanent wave processes.

When exposed to particularly aggressive demands, for example bleaching with oxidizing agents, such as hydrogen peroxide, in which the pigments distributed in the cortex are destroyed by oxidation, the inside of the hair can also be affected. If human hair is to be coloured permanently, in practice only oxidizing hair-colouring processes are possible. In the case of oxidative colouring of the hair, the dyestuff chromophores are formed by reaction of precursors (phenols, aminophenols and less frequently also diamines) and bases (usually p-phenylenediamine) with the oxidizing agent, usually hydrogen peroxide. Hydrogen peroxide concentrations of about 6% are usually used for this.

The process is usually based on a bleaching action by the hydrogen peroxide taking place, in addition to the colouring action. In human hair coloured by oxidation, as with bleached hair, microscopic holes are detectable at the points where melanin granules were present. It is a fact that the oxidizing agent hydrogen peroxide reacts not only with the colour precursors but also with the hair substance and as a result under certain circumstances can cause damage to the hair.

Washing the hair with aggressive surfactants can also make demands on the hair, and at least reduce its appearance or the appearance of the hairstyle overall. For example, certain water-soluble hair constituents (for example urea, uric acid, xanthine, keratin, glycogen, citric acid and lactic acid) can be leached out by washing the hair.

For these reasons, in some cases hair-care cosmetics which are intended to be rinsed out of the hair again after their action and in some cases those which are to remain on the hair have been used for a relatively long time. The latter can be formulated such that they not only care for the individual hair, but also improve the appearance of the hairstyle overall, for example by imparting to the hair more fullness, fixing the hairstyle over a longer period of time or improving its ease of styling.

For example, the combability of hair can be improved decisively by quaternary ammonium compounds. Such compounds are absorbed onto the hair and are often still detectable on the hair after the hair has been washed several times.

However, the prior art has lacked active compounds and formulations which satisfactorily provide care for damaged hair. Formulations which should give the hairstyle fullness have also often proved to be inadequate, or at least they were unsuitable for use as hair-care formulations. Formulations of the prior art which fix the hairstyle as a rule comprise, for example, viscous constituents, which run the risk of giving rise to a feeling of tackiness, which often has to be compensated by skilful formulation.

An object was therefore to remedy the disadvantages of the prior art.

Neither are examples for the preparation of transparent preparations of the water-in-oil type containing a low content of emulsifiers described, which produce white macroemulsions or white macroemulsion gels on moistened skin.

A particular object of the present invention was to provide gelatinous formulations based on finely dispersed systems of the water-in-oil type with the lowest possible emulsifier content which do not have the disadvatages of the prior art and which can have the most diverse cosmetic and/or dermatological applications, for example the uses described above. Another object of the invention was to enrich the limited range of gelatinous formulations based on finely dispersed systems of the water-in-oil type of the prior art.

It is known per se to prepare W/O microemulsion gels. WO 92/18147 describe W/O microemulsions which are converted into O/W microemulsions by adding water. However, the preparation of these W/O microemulsion gels requires a high emulsifier concentration. WO 94/22420 describes microemulsion gels which contain silicone oils and silicone emulsifiers (dimethicone copolyol and cyclomethicone/dimethicone) and are characterized by a high content of propylene glycol and glycerol. The gel is diluted with propellants, with the result that, following application to the skin, the propellant evaporates and a gel forms on the skin. This method of preparing microemulsion gels in the form of an aerosol did not indicate the route to the invention. U.S. Pat. No. 5,162,378 describes W/O microemulsions which contain, as emulsifiers, a mixture of 8–20% of cetyl dimethicone copolyols, polyglycerol esters and hexyl laurate. EP 216557 A2 describes translucent W/O microemulsions in which the oil phase is a mineral oil and the emulsifier is a polyglycerol ester. The transparency of these emulsions is achieved by matching the refractive indices of water and oily phase. U.S. Pat. No. 5,045,337 describes W/O microemulsions for the food-stuffs sector, which are characterized by very high contents of lipids (90–99.8%). The concentration of emulsifiers based on polyglycerol esters which are used can therefore be kept low since the amount of solubilized water is only from 0.1 to 5%.

In order to solubilize water-soluble active compounds, it is of particular advantage to micellize relatively large amounts of water in a cosmetic oily phase for a simultaneously low content of emulsifiers. It is noteworthy that the production of microemulsion gels for the cosmetics or dermatological sector using a low content of emulsifiers, relatively high concentration of solubilized water, broad variation possibility of the oil components and the crosslinking of water droplets by hydrophilically modified lipophilic polymers is not described.

It was the object to remedy these shortcomings.

Surprisingly, all of the objects on which the invention is based are achieved by microemulsions or microemulsion gels of the water-in-oil type having a low content of emulsifiers which produce white macroemulsions or white macroemulsion gels on moistened skin (showering, washing the face, body).

Surprisingly, all the objects on which the invention is based are achieved by microemulsion gels, (a) based on microemulsions of the water-in-oil type, which comprise
an oily phase, which is essentially composed of constituents of low volatility, and an aqueous phase comprising:
one or more polyethoxylated W/O emulsifiers and/or
one or more polypropoxylated W/O emulsifiers and/or
one or more polyethoxylated and polypropoxylated W/O emulsifiers, and/or
one or more monoesters, diesters, polyesters of polyols as W/O emulsifiers and/or
one or more monoethers, diethers, polyethers of polyols as W/O emulsifiers and/or
one or more dimethicone copolyols as W/O emulsifiers and/or one or more fatty alcohols or fatty acids and W/O emulsifiers and/or one or more sorbitan esters as W/O emulsifiers and/or one or more methylglucose esters as W/O emulsifiers if desired furthermore comprising one or more O/W emulsifiers obtainable by preparing a mixture of the base components, comprising the aqueous phase, the oily phase and one or more of the emulsifiers according to the invention, the HLB value of the emulsifier or of the emulsifier combination being in the range 2–14, (b) in which the droplets of the discontinuous aqueous phase are joined to one another by one or more crosslinking substances, the molecules of which are distinguished by at least one hydrophobic region, which has an extension which is capable of bridging the distance between the microemulsion droplets, and by at least one hydrophilic region, which is capable of entering into a hydrophilic interaction with the microemulsion droplets.

The percentages by weight of the emulsifiers are preferably <20%, very particularly preferably 0.1–10%, based on the total weight of the microemulsion.

It is equally advantageous here if the cross-linking substance, also called a thickener in the context of the present description, forms an independent gel network in which the microemulsion droplets are then held firmly by the hydrophobic interaction (so-called associated thickeners are then present), or if the network is held together by the crosslinking with the microemulsion droplets in the junctions of the network. In addition, the end groups of the hydrophobic polymer can also have ionic character and, for example, be carboxylates or sulphonates.

BRIEF DESCRIPTION OF THE DRAWINGS

FIG. 1 depicts water-in-oil microemulsion droplets joined by crosslinker molecules.

FIG. 1 illustrates this novel principle for W/O microemulsions: the microemulsion droplets of a W/O microemulsion, which are shown as shaded circles, are joined to one another by the crosslinker molecules, shown as lines, which carry hydrophilic radicals, symbolized by rectangles, at both ends. It can be seen that in principle a water droplet can also accommodate several hydrophilic radicals, as a result of which a higher degree of crosslinking and three-dimensionality of the network can be ensured.

The crosslinking substances used according to the invention as a rule follow structural diagrams as follows:

$$A—B—A \tag{1}$$

$$A—B—A \atop | \atop A \tag{2}$$

$$\begin{array}{c} A \\ | \\ A—B—A \\ | \\ A \end{array} \tag{3}$$

wherein B can symbolize a hydrophobic region of the particular crosslinker molecule and A in each case symbolizes hydrophilic regions, which can also be of different chemical nature within one molecule.

However, structural diagrams such as

 (4)

 (5)

 (6)

 (7)

 (8)

and analogously formed structures which are yet more complex also fall entirely within the context of the invention submitted here.

Structural diagrams as follows:

 (9)

 (10)

 (11)

 (12)

 (13)

wherein Z here is a central unit, which can be hydrophilic or hyrophobic and as a rule consists of an oligo- or polyfunctional molecular radical, also fall within the context of the invention submitted here.

Thickeners with a higher degree of branching of course also fall within the context of the present invention.

For example, Z in diagram (10) can consist of a glyceryl radical, the three OH functions of which pass into the regions B, which in their turn consist, for example, of (SiOMe$_2$) chains of equal or unequal length, and the terminal group of which is linked covalently to an ethoxylated group, for example. Further groups (alkyl, aryl, hetaryl, saturated, unsaturated) can also be inserted between the functional group (here an O atom) and the hydrophobic group (here SiOMe$_2$).

Partial substitution on the glycerol is also possible, as a result of which structures which correspond to diagram (9) form.

The hydrophobic groups B can advantageously be chosen such that the crosslinker overall is oil-soluble or at least dispersible in oil, in which case the hydrophilic content of the groups A should then be over-compensated.

The following more specific structure diagrams can be followed, for example, for structure diagram (1):

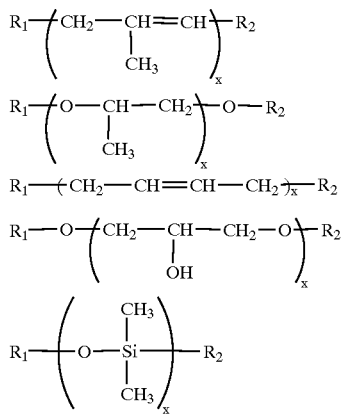

wherein $R_1$, $R_2$, independently of one another can be branched or unbranched, saturated or unsaturated, cyclic or chain-like aliphatic, aromatic or heteroaromatic radicals, which form the water-soluble/dispersible part of the polymer. These radicals can, for example, be polyols (e.g. sorbitol, glycerol, pentaerythritol, sucrose, polyglycerol), glucans, sugars, carboxylate groups, sulphonate groups, sulphate groups, aromatics or heteroaromatics or $SiR(OH)_n$ groups substituted by hydroxyl groups and/or sulphonic acid groups and/or carboxylate groups and/or sulphate groups. x is a number which allows the entire molecule to be soluble or at least dispersible in oil, typically chosen from the range greater than 10, advantageously from the range 20–5000. In the individual case x can also assume still considerably higher values, even several millions. This is known per se to the expert and requires no further explanation.

For the structure diagram (10) for example, the following more specific structure diagrams can be followed:

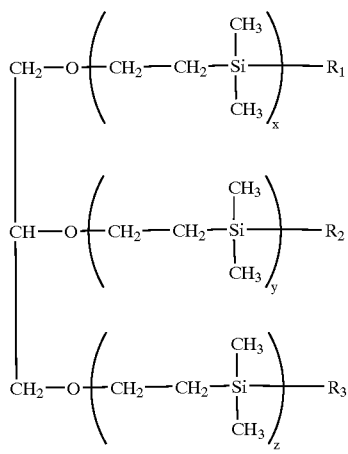

wherein $R_1$, $R_2$, $R_3$ independently of one another can be branched or unbranched, saturated or unsaturated, cyclic or chain-like aliphatic, aromatic or heteroaromatic radicals, which form the water-soluble/dispersible part of the polymer. These radicals can, for example, be polyols (e.g. glycerol, pentaerythritol, sucrose, polyglycerol), glucans, sugars, carboxylate groups, sulphonate groups, sulphate groups, aromatics or heteroaromatics or $SiR(OH)n$ groups substituted by hydroxyl groups and/or sulphonic acid groups and/or carboxylate groups and/or sulphate groups. x, y, z here are numbers which permit the entire molecule to be soluble or at least dispersible in oil, typically chosen from the range greater than 10, advantageously from the range 20–5000. Partial substitution is also possible here, it being possible for one or more of the indices x, y, z to assume the value zero and for one or more of the radicals $R_1$, $R_2$ or $R_3$ to be hydrogen atoms.

For structure diagram (11) for example, the following more specific structure diagrams can be followed:

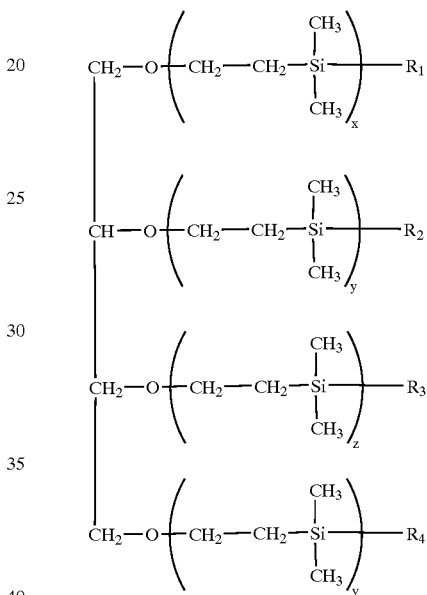

wherein $R_1$, $R_2$, $R_3$, $R_4$ independently of one another can be branched or unbranched, saturated or unsaturated, cyclic or chain-like aliphatic or aromatic radicals, which form the water-soluble/dispersible part of the polymer. These radicals can, for example, be polyols (glycerol, pentaerythritol, sucrose, polyglycerol), glucans, sugars, carboxylate groups, sulphonate groups, sulphate groups, aromatics or heteroaromatics or $SiR(OH)_n$ groups substituted by hydroxyl groups and/or sulphonic acid groups and/or carboxylate groups and/or sulphate groups. x, y, v and z here are numbers which permit the entire molecule to be soluble or at least dispersible in oil, typically chosen from the range greater than, 10, advantageously from the range 20–5000. It also goes without saying here that partial substitution is possible, it being possible for one or more of the indices x, y, z and v to assume the value zero and for one or more of the radicals $R_1$, $R_2$, $R_3$ or $R_4$ to be hydrogen atoms. The substances here of course change into other structure diagrams.

It is also advantageous to choose thickeners which have branches at the polymer ends so that dendrimers are obtained.

Crosslinkers which have proved to be particularly suitable are those chosen from the group consisting of hydrophilically substituted polyisoprenes dimethicone copolyols of the general formula. R—Si(CH$_3$)$_2$O—(Si(CH$_3$)$_2$O)$_n$—Si(CH$_3$)$_2$R', where R and R' independently of one another are branched or unbranched, saturated or unsaturated, cyclic or chain-like aliphatic, aromatic or heteroaromatic hydrophobic groups, to which hydrophilic groups are covalently bonded, so that overall the radicals R and R' are water-soluble or dispersible, which can have the structures given below for the hydrophilic groups. It is also possible to choose for R and R' exclusively hydrophilic groups without hydrophobic part-structures, where then R and R' independently of one another are branched or unbranched, saturated or unsaturated, cyclic or chain-like aliphatic, aromatic, heteroaromatic groups.

Preferred dimethicone copolyols have the general formula (A)

$$R\text{—}Si(CH_3)_2O\text{—}(Si(CH_3)_2O)_n\text{—}Si(CH_3)_2R',$$

where n is chosen such that the overall molecule is soluble/dispersible in fat and is preferably in the range $30\text{–}10^7$, and the radicals R and R' independently of one another have the following structural elements:

$$R, R' = (CH_2)_y\text{—}(O\text{—}CH_2\text{—}C(OH)H\text{—}CH_2)_xOH$$

$$R, R' = (CH_2)_y\text{—}(OC_2H_4)_x\text{—}OH$$

where y can, for example, have a value of $0\text{–}10^6$, preferably 1–30, in particular from 2 to 20, and x can, for example, have values from 1 to $10^7$, preferably from 2 to $10^6$, in particular from 3 to 500.

Particular preference is given to dimethicone copolyols of the above formula A in which R, R'=CH$_2$CH$_2$CH$_2$(OCH$_2$CH$_2$)$_{12}$OH, and n=148, and are termed A1 below.

Preferred hydrophilically substituted polyisoprenes have, for example, two ethyl oxide end groups or sulphate end groups or carboxylate end groups.

It can also be advantageous in some circumstances if the thickener(s) used according to the invention provides or provide physiological effectiveness in the sense of a cosmetic or pharmaceutical action. Thus, for example, the hydrophilic end groups of the polymer can carry the backbone of alginates.

The amount of thickeners according to the invention should preferably be in the range from 0.3 to 30% by weight, in particular from 1 to 10% by weight, in each case based on the total weight of the microemulsion.

The practice of preparing a microemulsion gel according to the invention accordingly advantageously comprises, after choosing suitable raw materials, i.e. the aqueous and oily phases, one or more W/O emulsifiers used according to the invention, one or more thickeners used according to the invention and, if appropriate, further substances, bringing together the individual components with stirring and obtaining said gels by cooling the mixture. During cooling, liquid crystalline regions or other phases familiar to the person skilled in the art may temporarily form. In addition, the thickener can also be subsequently added to a low viscosity W/O microemulsion obtained at room temperature or by cooling.

This process according to the invention is particularly suitable if heat-sensitive or readily volatile substances are to be incorporated into the W/O microemulsion gels according to the invention. Furthermore, this process, which is to be carried out at relatively low temperatures, is energy-saving compared with customary processes.

In the context of the present invention, particularly advantageous microemulsion gels are those (a) based on microemulsions of the water-in-oil type, which comprise a continuous oily phase and a discontinuous aqueous phase comprising at least one or more polyethoxylated W/O emulsifiers and/or one or more polypropoxylated W/O emulsifiers and/or one or more polyethoxylated and polypropoxylated W/O emulsifiers and/or one or more monoesters, diesters, polyesters of polyols as W/O emulsifiers and/or one or more monoethers of polyols and esters thereof as W/O emulsifiers and/or one or more sorbitan esters as W/O emulsifiers and/or one or more silicone emulsifiers as W/O emulsifiers and/or one or more fatty alcohols or fatty acids as W/O emulsifiers and/or one or more methylglucose esters as W/O emulsifiers, where this W/O emulsifier is chosen from the group consisting of fatty alcohol ethoxylates of the general formula R—O—(—CH$_2$—CH$_2$—O—)$_n$—H, where R is branched or unbranched alkyl, aryl or alkenyl radical, and n is a number from 1 to 10, polyethylene glycol ethers of the general formula R—O—(—CH$_2$—CH$_2$—O—)$_n$—R', where R and R' independently of one another are branched or unbranched alkyl or alkenyl radicals, and n is a number from 1 to 30, fatty acid ethoxylates of the general formula R—COO—(—CH$_2$—CH$_2$—O—)$_n$—H, where R is a branched or unbranched alkyl or alkenyl radical, and n is a number from 1 to 20, esterified fatty acid ethoxylates of the general formula R—COO—(—CH$_2$—CH$_2$—O—)$_n$—C(O)—R' where R and R' independently of one another are branched or unbranched alkyl or alkenyl radicals, and n is a number from 1 to 20, esterified fatty acid ethoxylates of the general formula R—COO—(—CH$_2$—CH$_2$—O—)$_n$—C(O)—R', where R and R' independently of one another are branched or unbranched alkyl, hydroxyalkyl or alkenyl radicals, and n is a number from 1 to 40, etherified fatty acid ethoxylates of the general formula R—COO—(—CH$_2$—CH$_2$—O—)$_n$—R', where R and R' independently of one another are branched or unbranched alkyl or alkenyl radicals, and n is a number from 1 to 40 fatty alcohol propoxylates of the general formula R—O—(—CH$_2$—CH(CH$_3$)—O—)$_n$—H, where R is a branched or unbranched alkyl or alkenyl radical, and n is a number from 1 to 30, polyoxyethylene sorbitan fatty acid esters based on branched or unbranched alkanoic or alkenoic acids and having a degree of ethoxylation of from 1 to 10, cholesterol ethoxylates having a degree of ethoxylation between 1 and 10, ethoxylated glycerides having a degree of ethoxylation of from 1 to 30, ethoxylated triglycerides having a degree of ethoxylation between 1 and 30, monoglycerol ethers of the type R—O—CH$_2$—C(H)OH—CH$_2$OH, where R is a branched or unbranched alkyl, aryl or alkenyl radical, and monoglycerol esters of the type RC(O)OCH$_2$—C(H)OH—CH$_2$OH where R is a branched or unbranched alkyl, hydroxyalkyl, aryl or alkenyl radical, diglycerol esters of the type RC(O)OCH$_2$—C(H)OH—CH$_2$OC(O)R', where R and R' independently of one another are branched or unbranched alkyl, hydroxyalkyl or alkenyl radicals, and n is a number from 1 to 30, polyglycerol mono- or di- or polyesters, where the fatty acids independently of one another are branched or unbranched alkyl, hydroxyalkyl or alkenyl radicals, pentaerythritol esters, where the fatty acids independently of one another are branched or unbranched alkyl, hydroxyalkyl or alkenyl radicals, propylene glycol esters, where the fatty acids independently of one another are branched or unbranched alkyl, hydroxyalkyl or alkenyl radicals, sorbitan esters, where the fatty acids independently of one another are branched or unbranched alkyl, hydroxyalkyl or alkenyl radicals, fatty alcohols R—OH and fatty acids RCOOH, where R is a branched or unbranched alkyl or alkenyl radical, silicone emulsifiers methylglucose esters, where the fatty acids independently of one another are branched or unbranched alkyl, hydroxyalkyl or alkenyl radicals, if desired comprising one or more O/W emulsifiers having a total emulsifier content of preferably less than 20% by weight, based on the total weight of the emulsion, obtainable by preparing a mixture of the base components, comprising aqueous phase, oily phase, one or more of the W/O emulsifiers according to the invention, if desired one or more O/W emulsifiers, where the HLB value of the emulsifier or of the emulsifier combination is in the range 2–14, (b) in which the droplets of the discontinuous aqueous phase are joined to one another by one or more crosslinking substances, the molecules of which are distinguished by at least one hydrophobic region which has an extension which is capable of bridging the distance between the microemulsion droplets, and by at least one hydrophilic region which is capable of entering into hydrophilic interaction with the microemulsion droplets.

According to the invention, the emulsifier/the emulsifier mixture is particularly advantageously used in a HLB range of 2–14.

From the group of monoglycerol esters of the type RC(O)OCH$_2$—C(H)OH—CH$_2$OH, it is advantageous to use glycerol isostearate or glycerol monocaprylate.

From the group of polyglycerol mono- or di- or polyesters, it is advantageous to use polyglycerol diisostearate (HLB=6.0) and polyglycerol triisostearate (HLB=4).

It is advantageous to choose the fatty alcohol ethoxylates from the group of ethoxylated stearyl alcohols, cetyl alcohols, cetylstearyl alcohols (cetearyl alcohols). Particular preference is given to: Polyethylene glycol (2) stearyl ether (steareth-2).

It is further advantageous to choose the fatty acid ethoxylates from the following group: polyethylene glycol(4) stearate.

Advantageous esterified fatty acid ethoxylates are polyethylene glycol(12) dilaurate, polyethylene glycol(8) distearate.

It is likewise favourable to choose the ethoxylated sorbitan esters from the group consisting of polyethylene glycol (20) sorbitan trioleate, polyethylene glycol(20) sorbitan triisostearate.

An advantageous ethoxylated cholesterol derivative which can be used is polyethylene glycol(5) soya sterol.

An advantageous ethoxylated triglyceride which can be used is polyethylene glycol(20) glycerol tristearate.

It is also advantageous to choose the polyethylene glycol glycerol fatty acid ester from the group polyethylene glycol (5) glyceryl stearate.

An advantageous monoglycerol ether is 2-ethylhexyl glycerol ether.

It is likewise favourable to choose diglycerol esters from the group of polyglyceryl-2 dipolyhydroxy fatty acid.

Sorbitan esters which have proven effective are sorbitan monolaurate and sorbitan monooleate.

O/W emulsifiers which can be employed as optional emulsifiers which are nevertheless advantageous according to the invention are: relatively highly ethoxylated fatty alcohols having from 8 to 30 carbon atoms, relatively highly ethoxylated diglycerol esters of saturated and/or unsaturated, branched and/or unbranched alkanecarboxylic acids having a chain length of from 8 to 24 carbon atoms, in particular 12–18 carbon atoms, relatively highly ethoxylated sorbitan esters of saturated and/or unsaturated, branched and/or unbranched alkanecarboxylic acids having a chain length of from 8 to 24 carbon atoms, in particular 12–18 carbon atoms.

relatively highly ethoxylated esterified fatty acid ethoxylates of saturated and/or unsaturated, branched and/or unbranched alkanecarboxylic acids having a chain length of from 8 to 24 carbon atoms, in particular 12–18 carbon atoms.

relatively highly ethoxylated polyethylene glycol glycerol fatty acids of saturated and/or unsaturated, branched and/or unbranched alkanecarboxylic acids having a chain length of from 8 to 24 carbon atoms, in particular 12–18 carbon atoms, relatively highly ethoxylated triglycerides of saturated and/or unsaturated branched and/or unbranched alkane carboxylic acids having a chain length of from 8 to 24 carbon atoms, in particular 12–18 carbon atoms.

And also polyglycerol mono- and diesters of saturated and/or unsaturated, branched and/or unbranched alkanecarboxylic acids having a chain length of from 8 to 24 carbon atoms, in particular 12–18 carbon atoms, or polyglycerol esters or ethers of methylglucose esters.

It is also possible to use anionic or cationic O/W emulsifiers such as, for example, the salts of alkyl ether carboxylic acids, acyl lactylate, acyl glutamate and acyl sarcosinate.

It is advantageous to use cetyltrimethylammonium bromide as cationic emulsifier.

It is advantageous to use, as anionic emulsifier, sodium lauroyl lactylate, sodium caproyl lactylate or sodium laureth sulphate.

From the group of polyglycerol mono- or di- or polyesters, it is advantageous to use polyglycerol monoisostearate (HLB=14).

The oily phase of the microemulsion gels according to the invention is advantageously chosen from the group consisting of esters of saturated and/or unsaturated, branched and/or unbranched alkanecarboxylic acids having a chain length of 3 to 30 C atoms and saturated and/or unsaturated, branched and/or unbranched alcohols having a chain length of 3 to 30 C atoms, and from the group consisting of esters of aromatic carboxylic acids and saturated and/or unsaturated, branched and/or unbranched alcohols having a chain length of 3 to 30 C atoms. Such ester oils can then advantageously be chosen from the group consisting of isopropyl myristate, isopropyl palmitate, isopropyl stearate, isopropyl oleate, n-butyl stearate, n-hexyl laurate, n-decyl oleate, isoocyl stearate, isononyl stearate, isononyl isononanate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and naturally occuring mixtures of such esters, for example jojoba oil.

The oily phase can furthermore advantageously be chosen from the group consisting of branched and unbranched hydrocarbons and waxes, silicon oils, dialkyl ethers and the group consisting of saturated or unsaturated, branched or unbranched alcohols, as well as fatty acid triglycerides, that is to say the triglycerol esters of saturated and/or unsaturated, branched and/or unbranched alkanecarboxylic acids having a chain length of 8 to 24, in particular 12–18 C atoms. The fatty acid triglycerides can advantageously be chosen, for example, from the group consisting of synthetic, semi-synthetic and naturally occurring oils, for example olive oil, sunflower oil, soya oil, groundnut oil, rape oil, almond oil, palm oil, coconut oil, palm kernel oil and so on.

Any desired mixtures of such oil and wax components can also advantageously be employed in the context of the present invention.

If appropriate, it may also be advantageous to add waxes to the oily phase.

The oily phase is advangaeously chosen from the group consisting of 2-ethylhexyl isostearate, octyldodecanol, isotridecyl isononanoate, isoeicosan, 2-ethylhexyl cocoate, $C_{12-15}$-alkyl benzoate, capryl/capric acid triglyceride and dicaprylyl ether.

Of the hydrocarbons, paraffin oil, squalane and squalene are advantageously to be used in the context of the present invention.

The oily phase can furthermore advantageously have a content of cyclic or linear silicone oils or consist completely of such oils.

Cyclomethicone (octamethylcyclotetrasiloxane) is advantageously employed as a silicone oil to be used according to the invention. However, other silicone oils can also advantageously be used in the context of the present invention, for example hexamethylcyclotrisiloxane, polydimethylsiloxane and poly(methylphenylsiloxane).

According to the invention it is possible to keep the total content of emulsifiers less than 15% by weight, based on the total weight of the microemulsion gels according to the invention. It is preferable to keep the total content of emulsifiers below 10% by weight, in particular below 8% by weight, based on the total weight of the microemulsion gels. In the individual case, it is possible here that the concentrations are slightly above or below the above-mentioned limits, and nevertheless the emulsion types in question are obtained. In view of the widely scattered diversity of suitable emulsifiers and oil constituents, this is not unexpected to the expert, so that he knows that falling above or below such limits does not depart from the basis of the present invention.

The microemulsion gels according to the invention advantageously comprise electrolytes, in particular one or more salts with the following anions: chlorides, and furthermore inorganic oxo-element anions, and of these in particular sulphates, carbonates, phosphates, borates and aluminates. Electrolytes based on organic anions can also advantageously be used, for example lactates, acetates, benzoates, propionates, tartrates, citrates and many others. Comparable effects can also be achieved by ethylenediaminetetraacetic acid and salts thereof.

Cations of the salts which are preferably used are ammonium, alkylammonium, alkali metal, alkaline earth metal, magnesium, iron and zinc ions. It does not need mentioning that in cosmetics, only physiologically acceptable electrolytes should be used. Special medical uses of the microemulsions according to the invention, on the other hand, can at least in principle necessitate the use of electrolytes which should not be used without medical supervision.

Potassium chloride, sodium chloride, magnesium sulphate, zinc sulphate and mixtures thereof are particularly preferred. Salt mixtures such as occur in natural salt from the Dead Sea are also advantageous.

The concentration of the electrolyte or electrolytes should be about 0.1–10.0% by weight, particularly advantageously about 0.3–8.0% by weight, based on the total weight of the formulation.

The microemulsion gels according to the invention furthermore outstandingly help to smooth the skin, especially if they are provided with one or more substances which promote smoothing of the skin.

If the microemulsion gels according to the invention are bases for cosmetic deodorants/anti-perspirants, all the customary active compounds can advantageously be used, for example odour maskers, such as the customary perfume constituents, odour absorbers, for example the laminar silicates described in the Laid-Open Specification DE-P 40 09 347, and of these in particular montmorillonite, kaolinite, ilite, beidellite, nontronite, saponite, hectorite, bentonite and smectite, and furthermore, for example, zinc salts of ricinoleic acid. Germ-inhibiting agents are also capable of being incorporated into the microemulsions according to the invention. Advantageous substances are, for example, 2,4,4'-trichloro-2'-hydroxydiphenyl ether (Irgasan), 1,6-di-(4-chlorophenylbiguanido)hexane (chlorhexidine), 3,4,4'-trichlorocarbanilide, quaternary ammonium compounds, oil of cloves, mint oil, oil of thyme, triethyl citrate, farnesol (3,7,11-trimethyl-2,6,10-dodecatrien-1-ol) and the active agents described in the Patent Laid-Open Specifications DE-37 40 186, DE-39 38 140, DE-42 04 321, DE-42 29 707, DE-42 29 737, DE-42 37 081, DE-43 09 372 and DE-43 24 219.

The customary antiperspirant active compounds can also advantageously be used in the microemulsion gels according to the invention, in particular astringents, for example basic aluminium chlorides.

The cosmetic deodorants according to the invention can be in the form of aerosols, that is to say preparations which can be sprayed from aerosol containers, squeeze bottles or by a pump device, or in the form of liquid compositions which can be applied by means of roll-on devices, but also in the form of microemulsion gels which can be applied from normal bottles and containers.

Suitable propellants for cosmetic deodorants according to the invention which can be sprayed from aerosol containers are the customary known readily volatile liquefied propellants, for example hydrocarbons (propane, butane or isobutane), which can be employed by themselves or as a mixture with one another. Compressed air can also advantageously be used.

The expert of course knows that there are propellant gases which are non-toxic per se and would be suitable in principle for the present invention, but which should nevertheless be omitted because of an unacceptable action on the environment or other concomitant circumstances, in particular chlorofluorohydrocarbons (CFCs).

Those cosmetic and dermatological formulations which are in the form of a sunscreen composition are also favourable. These advantageously additionally comprise, in addition to the active compound combinations according to the invention, at least one UVA filter substance and/or at least one UVB filter substance and/or at least one inorganic pigment.

However, it is also advantageous in the context of the present invention to provide those cosmetic and dermatological formulations of which the main purpose is not protection from sunlight but which nevertheless comprise a content of UV protection substances. Thus, for example, UV-A or UV-B filter substances are usually incorporated into day creams.

Formulations according to the invention can advantageously comprise substances which absorb UV radiation in the UVB range, the total amount of the filter substances being, for example, 0.1% by weight to 30% by weight, preferably 0.5 to 10% by weight, in particular 1 to 6% by weight, based on the total weight of the formulations.

The UVB filters can be oil-soluble or water-soluble. Examples of oil-soluble substances which may be mentioned are, for example:

3-benzylidenecamphor and derivatives thereof, for example 3-(4-methylbenzylidene)camphor;

4-aminobenzoic acid derivatives, preferably 2-ethylhexyl 4-(dimethylamino)-benzoate and amyl 4-(dimethylamino)benzoate;

esters of cinnamic acid, preferably 2-ethylhexyl 4-methoxycinnamate and isopentyl 4-methoxycinnamate;

esters of salicylic acid, preferably 2-ethylhexyl salicylate, 4-isopropylbenzyl salicylate and homomenthyl salicylate;

derivatives of benzophenone, preferably 2-hydroxy-4-methoxybenzophenone, 2-hydroxy-4-methoxy-4'-methyl-benzophenone and 2,2'-dihydroxy-4-methoxybenzo-phen esters of benzalmalonic acid, preferably di(2-ethyl-hexyl) 4-methoxybenzalmalonate; and 2,4,6-trianilino-(p-carbo-2'-ethyl-1'-hexyloxy)-1,3,5-triazine.

Advantageous water-soluble substances are:

2-phenylbenzimidazole-5-sulphonic acid and salts thereof, for example sodium, potassium or triethanolammonium salts, sulphonic acid derivatives of benzophenones, preferably 2-hydroxy-4-methoxybenzophenone-5-sulphonic acid and its salts;

sulphonic acid derivatives of 3-benzylidenecamphor, such as, for example, 4-(2-oxo-3-bornylidenemethyl)-benzenesulphonic acid, 2-methyl-5-(2-oxo-3-bornylidenemethyl)benzenesulphonic acid and their salts.

The list of UVB filters mentioned, which can be used according to the invention, is of course not intended to be limiting.

The invention also relates to the combination of a UVA filter according to the invention with a UVB filter, and a cosmetic or dermatological formulation according to the invention which also comprises a UVB filter.

It may also be advantageous to employ UVA filters which are usually contained in cosmetic and/or dermatological formulations in formulations according to the invention. Such substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)propane-1,3-dione. The invention also relates to formulations which comprise these combinations. The same amounts of UVA filtersubstances as have been mentioned for UVB filter substances can be used.

Cosmetic and/or dermatological formulations according to the invention can also comprise inorganic pigments which are usually used in cosmetics for protecting the skin from UV rays. These are oxides of titanium, zinc, iron, zirconium, silicon, manganese, aluminium and cerium and mixtures thereof, as well as modifications in which the oxides are the active agents. The pigments are particularly preferably those based on titanium dioxide. The amounts mentioned for the above combinations can be used.

An surprising property of the present invention is that formulations according to the invention are very good vehicles for cosmetic or dermatological active compounds in the skin, advantageous active compounds being antioxidants which can protect the skin from oxidative stress.

According to the invention, the formulations advantageously comprise one or more antioxidants. Favourable antioxidants, which are nevertheless to be used optionally, are all the antioxidants which are suitable or customary for cosmetic and/or dermatological applications. It is advantageous here to use antioxidants as the sole class of active compound, for example if a cosmetic or dermatological use such as combating oxidative stress of the skin is a priority. However, it is also favourable to provide the microemulsion gels according to the invention with a content of one or more antioxidants if the formulations are to serve another purpose, for example as deodorants or sunscreen compositions.

The antioxidants are particularly advantageously chosen from the group consisting of amino acids (for example histidine, tyrosine and tryptophan) and derivatives thereof, imidazoles (for example urocanic acid) and derivatives thereof, peptides, such as D,L-carnosine, D-carnosine, L-carnosine and derivatives thereof (for example anserine), carotenoids, carotenes (for example α-carotene, β-carotene and lycopene) and derivatives thereof, liponic acid and derivatives thereof (for example dihydroliponic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, gammalinoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (for example buthionine-sulphoximines, homocysteine-sulphoximine, buthionine-sulphones and penta-, hexa- and heptathionine-sulphoximine) in very low tolerated dosages (for example pmol to μmol/kg), and furthermore (metal) chelators (for example α-hydroxy-fatty acids, α-hydroxypalmitic acid, phytic acid and lactoferrin), α-hydroxy acids (for example citric acid, lactic acid and malic acid), humic acid, bile acid, bile extracts, bilirubin, biliverdin, EDTA, EGTA and derivatives thereof, unsaturated fatty acids and derivatives thereof (for example gamma-linolenic acid, linoleic acid and oleic acid), folic acid and derivatives thereof, ubiquinone and ubiquinol and derivatives thereof, vitamin C and derivatives (for example ascorbyl palmitates, Mg ascorbyl phosphates and ascorbyl acetates), tocopherols and derivatives (for example vitamin E acetate), vitamin A and derivatives (vitamine A palmitate) and coniferyl benzoate of benzoin resin, rutic acid and derivatives thereof, ferulic acid and derivatives thereof, butylhydroxytoluene, butylhydroxyanisole, nordihydroguaiac resin acid, nordihydroguaiaretic acid, trihydroxybutyrophenone, uric acid and derivatives thereof, zinc and derivatives thereof (for example ZnO and $ZnSO_4$), selenium and derivatives thereof (for example seleniummethionine), stilbenes and derivatives thereof (for example stilbene oxide and trans-stilbene oxide) and the derivatives of these active compounds mentioned which are suitable according to the invention (salts, esters, ethers, sugars, nucleotides, nucleosides, peptides and lipids).

Water-soluble antioxidants can particularly advantageously be employed in the context of the present invention.

The amount of antioxidants (one or more compounds) in the formulations is preferably 0.001 to 30% by weight, particularly preferably 0.05–20% by weight, in particular 1–10% by weight, based on the total weight of the formulation.

If vitamin E and/or derivatives thereof are the antioxidant or antioxidants, it is advantageous to choose the particular concentrations thereof from the range of 0.001–10% by weight, based on the total weight of the formulation.

If vitamin A or vitamin A derivatives or carotenes or derivatives thereof are the antioxidant or antioxidants, it is advantageous to choose the particular concentrations thereof from the range of 0.001–10% by weight, based on the total weight of the formulation.

It is of course known to the expert that high-quality cosmetic formulations are usually inconceivable without the customary auxiliaries and additives. These include, for example, agents which impart consistency, fillers, perfume, dyestuffs, emulsifiers, additional active compounds, such as vitamins or proteins, light protection agents, stabilizers, insect repellants, alcohol, water, salts and substances having an antimicrobial, proteolytic or keratolytic action.

According to the invention, the active compounds can also very advantageously be chosen from the group consisting of lipophilic active compounds, in particular from the following group:

acetylsalicylic acid, atropine, azulene, hydrocortisone and derivatives thereof, for example hydrocortisone 17-valerate, vitamins, for example ascorbic acid and derivatives thereof, vitamins of the B and D series, very favourably vitamin $B_1$, vitamin $B_{12}$ and vitamin $D_1$, but also bisabolol, unsaturated fatty acids, that is to say the essential fatty acids (often also called vitamin F), in particular γ-linolenic acid, oleic acid, eicosapentanoic acid, docosahexanoic acid and derivatives thereof, chloramphenicol, caffeine, prostaglandins, thymol, camphor, extracts or other products of plant and animal origin, for example oil of evening primrose, borret oil or current kernel oil, fish oils and cod-liver oil, and also ceramides and ceramide-like compounds and so on.

Although the use of hydrophilic active compounds is of course also favoured according to the invention, it is another advantage of the microemulsion gels according to the invention that the high number of very finely divided droplets renders precisely oil-soluble or lipophilic active compounds biologically available with a particularly high activity.

It is also advantageous to choose the active compounds from the group of re-oiling substances, for example Purcellin oil, Eucerit® and Neocerit®.

It is also possible, and may be advantageous, to add wash-active surfactants to the formulations according to the invention. Aqueous cosmetic cleansing agents according to the invention or low-water or anhydrous cleansing agent concentrates intended for aqueous cleansing can comprise cationic, anionic, nonionic and/or amphoteric surfactants, for example conventional soaps, for example fatty acid salts of sodium, alkyl sulphates, alkyl ether sulphates, alkane- and alkylbenzenesulphonates, sulphoacetates, sulphobetaines, sarcosinates, amidosulphobetaines, sulphosuccinates, sulphosuccinic acid half-esters, alkyl ether-carboxylates, protein-fatty acid condensates, alkylbetaines and aminobetaines, fatty acid alkanolamides and polyglycol ether derivatives.

Cosmetic formulations which are cosmetic cleansing formulations for the skin can be present in liquid or solid form. They preferably comprise at least one anionic, nonionic or amphoteric surface-active substance or mixtures thereof, at least one electrolyte according to the invention and auxiliaries such as are usually used for this purpose. The surface-active substance can preferably be present in the cleansing formulations in a concentration of between 1 and 50% by weight, based on the total weight of the formulations.

Cosmetic formulations which are a shampooing agent preferably comprise at least one anionic, nonionic or amphoteric surface-active substance or mixtures thereof, if appropriate electrolytes and auxiliaries such as are usually used for this purpose. The surface-active substance can preferably be present in the cleansing formulations in a concentration of between 1 and 50% by weight, based on the total weight of the formulations. Cetyltrimethylammonium salts, for example, are advantageously to be used.

The compositions according to the invention intended for cleansing the hair or the skin comprise, in addition to the abovementioned surfactants, water and, if appropriate, the additives customary in cosmetics, for example perfume, thickeners, dyestuffs, deodorants, antimicrobial substances, re-oiling agents, complexing and sequestering agents, pearlescent agents, plant extracts, vitamins, active compounds and the like.

In spite of their oil content, the formulations according to the invention surprisingly have a high cleansing power and have a highly regenerating or moisturizing action in respect of the general state of the skin. In particular, the formulations according to the invention have the effect of smoothing the skin, reduce the dryness sensation of the skin and make the skin supple.

If the microemulsion gels according to the invention are to be employed for hair care, they can comprise the customary constituents, usually, for example, film-forming polymers. Suitable such polymers having at least partly quaternized nitrogen groups (called "film-forming agents" below) are preferably those which are chosen from the group consisting of substances which, according to INCI nomenclature (International Nomenclature of Cosmetic Ingredients) carry the name

| | |
|---|---|
| Polyquaternium-2 | (Chemical Abstracts No. 63451-27-4, for example Mirapol ® A-15) |
| Polyquaternium-5 | (Copolymer of acrylamide and β-methacryloxyethyltrimethylammonium methosulphate, CAS No. 26006-22-4) |
| Polyquaternium-6 | (Homopolymer of N,N-dimethyl-N-2-propenyl-2-propene-1-aminium chloride, CAS No. 26062-79-3, for example Merquat ® 100 |
| Polyquaternium-7 | N,N-Dimethyl-N-2-propenyl-2-propene-1-aminium chloride, polymer with 2-propenamide, CAS No. 26590-05-6, for example Merquat ® S |
| Polyquaternium-10 | Quaternary ammonium salt of hydroxyethylcellulose, CAS No. 53568-66-4, 55353-19-0, 54351-50-7, 68610-92-4, 81859-24-7, for example Celquat ® SC-230M |
| Polyquaternium-11 | Vinylpyrrolidone/dimethylaminoethyl methacrylate copolymer/diethyl sulphate reaction product, CAS No. 53633-54-8, for example Gafquat 755N |
| Polyquaternium-16 | Vinylpyrrolidone/vinylimidazolinium methochloride copolymer, CAS No. 29297-55-0, for example Luviquat ® HM 552 |

| | |
|---|---|
| Polyquaternium-17 | CAS No. 90624-75-2, for example Mirapol ® AD-1 |
| Polyquaternium-19 | Quaternized water-soluble polyvinyl alcohol |
| Polyquaternium-20 | Water-dispersible quaternized polyvinyl octadecyl ether |
| Polyquaternium-21 | Polysiloxane-polydimethyl-dimethyl-ammonium acetate copolymer, for example Abil ® B 9905 |
| Polyquaternium-22 | Dimethyldiallylammonium chloride/acrylic acid copolymer, CAS No. 53694-7-0, for example Merquat ® 280 |
| Polyquaternium-24 | Polymeric quaternium ammonium salt of hydroxyethylcellulose, reaction product with an epoxide substituted by lauryl dimethylammonium, CAS No. 107987-23-5, for example Quatrisoft ® LM-200 |
| Polyquaternium-28 | Vinylpyrrolidone/methacrylamido-propyltrimethylammonium chloride copolymer, for example Gafquat ® HS-100 |
| Polyquaternium-29 | For example Lexquat ® CH |
| Polyquaternium-31 | CAS No. 136505-02-7, for example Hypan ® QT 100 |
| Polyquaternium-32 | N,N,N-Trimethyl-2-[(2-methyl-1-oxo-2-propenyl) oxy] ethanaminium chloride, polymer with 2-propeneamide, CAS No. 35429-19-7 |
| Polyquaternium-37 | CAS No. 26161-33-1 |

Formulations according to the invention for hair care advantageously comprise 0.2–50% by weight of one or more film-forming agents, preferably 5–30% by weight, in particular 10–25% by weight, in each case based on the total weight of the formulations. Such embodiments of the formulations according to the invention care for hair damaged or worn out by environmental influences, or protect against such environmental influences. The formulations according to the invention furthermore impart to the hairstyle a loose fullness and firmness, without having a tacky effect.

Where appropriate, it is possible and advantageous to use the formulations according to the invention as a base for pharmaceutical formulations. *Mutatis mutandis*, appropriate requirements apply to the formulation of medical formulations. The transitions between pure cosmetics and pure pharmaceuticals are continuous here. All active compound classes are in principle suitable according to the invention as pharmaceutical active compounds, liphophilic active compounds being preferred. Examples are: antihistamines, antiphlogistics, antibiotics, antimycotics, active compounds which promote circulation, keratolytics, hormones, steroids, vitamins and the like.

The cosmetic and dermatological formulations according to the invention can comprise cosmetic auxiliaries such as are usually used in such formulations, for example preservatives, bactericides, virucides, perfumes, substances for preventing foaming, dyestuffs, pigments which have a colouring action, other thickening agents which do not fall under the definition of the thickeners according to the invention, surface-active substances, emulsifiers, softening, humidifying and/or humectant substances, antiinflammatory substances, medicaments, fats, oils, waxes or other customary constituents of a cosmetic or dermatological formulation, such as alcohols, polyols, polymers, foam stabilizers, electrolytes and organic solvents.

Mixtures of the abovementioned solvents are particularly advantageously used.

Other constituents which can be used are fats, waxes and other naturally occurring and synthetic fatty substances, preferably esters of fatty acids with alcohols of low C number, for example with isopropanol, propylene glycol or glycerol, or esters of fatty alcohols with alkanoic acids of low C number or with fatty acids, alcohols, diols or polyols of low C number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

The microemulsion gels according to the invention are prepared, for example, by the following methods:

a) The emulsifier or the emulsifier combination is added to the oily phase at room temperature, and the mixture is stirred. It is advantageous to warm the mixture if solid ingredients are added. The aqueous phase, which is at RT, is added in portions with stirring to this microemulsion, which is at RT. The thickener according to the invention is added to this microemulsion with stirring to give a gel. If the thickener is not readily soluble, it can also be added to the oily phase from the start.

b) The emulsifier or the emulsifier combination according to the invention is added to the oily phase, and the mixture is heated in a range of, for example, 40–85° C. The aqueous phase, which has a temperature of 40–85° C., is added to this mixture in portions, and the whole is then cooled to RT. The thickener can be added at any point in the preparation.

c) Only some of the oily phase is added to the emulsifier/emulsifier combination. Water is then added in portions, and the resulting W/O microemulsion or the obtainable microemulsion gel is then diluted with the remainder of the oily phase. Other colloid-chemical phases (lamellar phases, hexagonal phases, inverse hexagonal phases, cubic phases etc.) can also temporarily form as intermediates.

Unless stated otherwise, all amounts, percentages or parts refer to the weight, in particular to the total weight of the preparations or of the respective mixture.

The following examples are intended to illustrate the present invention.

Preparation procedure for the crosslinkers of the group of hydrophilically substituted polyisoprenes:

| | |
|---|---|
| PI = | polyisoprene |
| PEG = | polyethylene glycol |
| PS = | polystyrene |

The numbers refer to the molecular weight.

a)

Polyisoprene with ethylene oxide end groups (PI-50,000 (PEG-5000)$_2$): isoprene was dried over calcium chloride for 12 hours and then distilled under argon. Directly prior to polymerization, purification over phenylmagnesium chloride is carried out. The purified monomer is stored in an ampoule over argon. Ethylene oxide is purified in the same way. The polymerization is carried out in a glass reactor under argon. Dried tetrahydrofuran is used as solvent. The polymerization is initiated using potassium naphthalide at −40° C. After 3 h, ethylene oxide is added. After two hours the temperature is increased to 60° C., and the mixture is stirred overnight. The reaction is terminated with methacryloyl chloride. The polymer is purified by repeated precipitation from methanol and then dried under reduced pressure. The molecular weights of the ABA triblock polymer determined by light scattering and gel permeation chromatography give the following values:

Polyisoprene: 50,000 g/mol

Polyethylene oxide: 5000 g/mol.

b)

Further ABA triblock copolymers were also prepared by varying the initiator/monomer ratio according to this procedure.

(PI-50,000 (PEG-10,000)$_2$):

Polyisoprene: 50,000 g/mol

Polyethylene oxide: 10,000 g/mol.

c)

Further ABA triblock copolymers were also prepared by varying the initiator/monomer ratio according to this procedure.

(PI-50,000 (PEG-20,000)$_2$):

Polyisoprene: 50,000 g/mol

Polyethylene oxide: 20,000 g/mol.

d)

Further ABA triblock copolymers were also prepared by varying the initiator/monomer ratio according to this procedure.

PI-39,000 (PEG-10,000)$_2$

Polyisoprene: 39,000 g/mol

Polyethylene oxide: 10,000 g/mol

Polyisoprene with ionic end group (SO$_3$—):

The preparation is analogous to the above instructions as far as the production of the polyisoprene anion. The anionic ends are reacted in equimolar amounts with 1,1-diphenylethane (distilled over sodium), and the solution is cooled to 168 K (tetrahydrofuran/liq. nitrogen), and an excess of 1,3-propane sultone is added. The solution is slowly brought to room temperature. Work-up is carried out in an analogous manner to that for the bis-polyethylene oxide-modified polyisoprene.

The counter ion can be varied by using potassium or lithium in the start reaction.

PI (SO$_3$Li)$_2$ (20,000 g/mol)

PI (SO$_3$Na)$_2$ (50,000 g/mol)

Polyisoprene with ionic carboxylate end group:

Gamma-butyrolactone is used instead of 1,3-propanesultone in the above procedure.

PI (CO$_2$Na)$_2$ (65,000 g/mol)

The following numerical data is % by weight. Examples 1 to 11 relate to low viscosity microemulsions according to the invention, and Examples 12 to 22 contain the microemulsion gels according to the invention.

The dimethicone copolyol used is defined unambiguously in the description with A1 as thickener or crosslinker.

EXAMPLE 1

W/O Microemulsion, Low Viscosity (Pumpspray, Deodorant Spray Concentrate)

| | |
|---|---|
| PEG-5 soya sterol | 4.70 |
| Sodium lauroyl lactylate | 2.30 |
| Dicaprylyl ether | 60.0 |
| Water | 33.0 |

EXAMPLE 2

W/O Microemulsion, Low Viscosity (Anti-acne Solution)

| | |
|---|---|
| PEG-5 soya sterol | 4.70 |
| Sodium lauroyl lactylate | 2.30 |
| Dicaprylyl ether | 60.0 |
| Water | 33.0 |

EXAMPLE 3

W/O Microemulsion, Low Viscosity (Deodorizing Body Lotion)

| | |
|---|---|
| Glyceryl isostearate | 5.00 |
| Sodium lauroyl lactylate | 2.00 |
| Dicaprylyl ether | 60.0 |
| Water | 33.0 |

EXAMPLE 4

W/O Microemulsion, Low Viscosity (After Shave Lotion)

| | |
|---|---|
| 2-Ethylhexyl glycerol ether | 6.00 |
| Sodium lauroyl lactylate | 1.00 |
| Dicaprylyl ether | 60.0 |
| Water | 33.0 |

EXAMPLE 5

W/O Microemulsion, Low Viscosity (Eye Make-up Remover Lotion)

| | |
|---|---|
| PEG-5 soya sterol | 3.50 |
| Sodium caproyl lactylate | 3.50 |
| Dicaprylyl ether | 60.0 |
| Water | 33.0 |

EXAMPLE 6

W/O Microemulsion, Low Viscosity (Shaving Lotion)

| | |
|---|---|
| Sodium lauroyl lactylate | 5.00 |
| Glyceryl caprylate | 2.00 |
| Dicaprylyl ether | 60.0 |
| Water | 33.0 |

EXAMPLE 7

W/O Microemulsion, Low Viscosity (Lotion for Dry Skin)

| | |
|---|---|
| Sodium lauroyl lactylate | 5.00 |
| Glyceryl caprylate | 2.00 |
| Dicaprylyl ether | 60.0 |
| Water | 33.0 |

EXAMPLE 8

W/O Microemulsion, Low Viscosity (Shower Lotion)

| | |
|---|---|
| 2-Ethylhexyl glycerol ether | 4.43 |
| Sodium laureth sulphate | 1.77 |
| Dicaprylyl ether | 53.09 |
| Water | 40.71 |

EXAMPLE 9

W/O Microemulsion, Low Viscosity (Base for Antiperspirant Lotion, Enzymes, Protein)

| | |
|---|---|
| Polyglycerol monoisostearate (Polydermanol GE 14 DA) | 5.00 |
| Polyglycerol diisostearate (Polydermanol GE 60 DS) | 2.00 |
| Isopropyl myristate | 60.0 |
| Water | 32.0 |

EXAMPLE 10

W/O Microemulsion, Low Viscosity (Base for Vitamin C, Water-soluble UV Filters

| | |
|---|---|
| Polyglycerol triisostearate (Polydermanol GE 40 DS) | 5.88 |
| PEG (15) cetyl ether | 2.35 |
| Isopropyl myristate | 70.59 |
| Water | 21.18 |

EXAMPLE 11

W/O Microemulsion, Low Viscosity (Hair Lotion, Hair Spray Concentrate)

| | |
|---|---|
| Cetyltrimethylammonium bromide | 1.10 |
| 2-Ethylhexyl glycerol ether | 6.90 |
| Dioctylcyclohexane | 69.0 |
| Water | 23.0 |

EXAMPLE 12

W/O Microemulsion, Gel (Deodorant Gel)

| | |
|---|---|
| PEG-5 soya sterol | 4.70 |
| Sodium lauroyl lactylate | 2.30 |
| Dicaprylyl ether | 52.02 |
| Water | 33.0 |
| PI-50,000 (PEG-5000)$_2$ | 7.98 |

EXAMPLE 13

W/O Microemulsion, Gel (Anti-acne Gel, Shaving Gel Concentrate)

| | |
|---|---|
| PEG-5 soya sterol | 4.70 |
| Sodium lauroyl lactylate | 2.30 |
| Dicaprylyl ether | 53.0 |
| Water | 33.0 |
| PI (SO$_3$Li)$_2$ (20,00 g/mol) | 7.00 |

EXAMPLE 14

W/O Microemulsion, Gel (Shaving Foam Base)

| | |
|---|---|
| Glyceryl isostearate | 5.00 |
| Sodium lauroyl lactylate | 2.00 |
| Dicaprylyl ether | 52.9 |
| Water | 33.0 |
| PI (CO$_2$Na)$_2$ (65,000 g/mol) | 7.10 |

EXAMPLE 15

W/O Microemulsion, Gel (After Shave Gel)

| | |
|---|---|
| 2-Ethylhexyl glycerol ether | 6.00 |
| Sodium lauroyl lactylate | 1.00 |
| Dicaprylyl ether | 52.60 |
| Water | 33.0 |
| PI-39,000 (PEG-10,000)$_2$ | 7.40 |

EXAMPLE 16

W/O Microemulsion, Gel (Eye Make-up Remover Gel)

| | |
|---|---|
| PEG-5 soya sterol | 3.50 |
| Sodium caproyl lactylate | 3.50 |
| Dicaprylyl ether | 52.72 |
| Water | 33.0 |
| PI-50,000 (PEG-10,000)$_2$ | 7.28 |

EXAMPLE 17

W/O Microemulsion, Gel (Skincare Gel)

| | |
|---|---|
| Sodium lauroyl lactylate | 5.00 |
| Glyceryl caprylate | 2.00 |
| Dicaprylyl ether | 52.72 |
| Water | 33.0 |
| PI-50,000 (PEG-20,000)$_2$ | 7.28 |

EXAMPLE 18

W/O Microemulsion, Gel (Gel for Dry Skin)

| | |
|---|---|
| Sodium lauroyl lactylate | 5.00 |
| Glyceryl caprylate | 2.00 |
| Dicaprylyl ether | 53.9 |
| Water | 33.0 |
| PI (SO$_3$Li)$_2$ (20,000 g/mol) | 6.40 |

EXAMPLE 19

W/O Microemulsion, Gel (Shower Gel)

| | |
|---|---|
| 2-Ethylhexyl glycerol ether | 4.43 |
| Sodium laureth sulphate | 1.77 |
| Dicaprylyl ether | 45.59 |
| PI-50,000 (PEG-5000)$_2$ | 7.50 |
| Water | 40.71 |

EXAMPLE 20

W/O Microemulsion, Gel (Antiperspirant Base, Gel for the Solubilization of Enzymes, Proteins)

| | |
|---|---|
| Polyglycerol monoisostearate (Polydermanol GE 14 DA) | 5.00 |
| Polyglycerol diisostearate (Polydermanol GE 60 DS) | 2.00 |
| Isopropyl myristate | 60.0 |
| PI-50,000 (PEG-10,000)$_2$ | 7.50 |
| Water | 32.0 |

EXAMPLE 21

W/O Microemulsion, Gel (Base for Vitamin C, Water-soluble UV Filters)

| | |
|---|---|
| Polyglycerol triisostearate (Polydermanol GE 40 DS) | 5.88 |
| PEG (15) cetyl ether | 2.35 |
| Isopropyl myristate | 63.09 |
| Dimethicone copolyol A1 (Goldschmidt) | 7.50 |
| Water | 21.18 |

EXAMPLE 22

W/O Microemulsion, Gel (Hair Gel)

| | |
|---|---|
| Cetyltrimethylammonium bromide | 1.10 |
| 2-Ethylhexyl glycerol ether | 6.90 |
| Dioctylcyclohexane | 62.00 |
| PI-50,000 (PEG-10,000)$_2$ | 7.00 |
| Water | 23.0 |

W/O Microemulsions Without Thickener (Examples 23–29)

EXAMPLE 23

| | |
|---|---|
| PEG-20 sorbitan monolaurate | 2.15 |
| Polyglycerol triisostearate (Polydermanol GE 40 DS) | 5.38 |
| Isopropyl myristate | 64.47 |
| Water | 28 |

EXAMPLE 24

| | |
|---|---|
| Polyglycerol diisostearate | 7.45 |
| Isopropyl myristate | 63.82 |
| Water | 28.73 |

EXAMPLE 25

| | |
|---|---|
| Steareth-2 | 5.66 |
| Steareth-16 | 2.77 |
| Cetearyl isononanoate | 72.29 |
| Water | 19.28 |

EXAMPLE 26

| | |
|---|---|
| PEG-20 octyl dodecyl ether | 4.12 |
| Ethylhexyl glycerol ether | 4.12 |
| Dicaprylyl ether | 70.58 |
| Water | 21.18 |

EXAMPLE 27

| | |
|---|---|
| Sorbitan laurate | 3.53 |
| PEG-20 sorbitan trioleate | 4.71 |
| Dicaprylyl ether | 70.58 |
| Water | 21.18 |

EXAMPLE 28

| Glyceryl isostearate | 3.0 |
|---|---|
| PEG-12 distearate | 4.0 |
| Dicaprylyl ether | 60.0 |
| Water | 33.0 |

EXAMPLE 29

| Lecithin | 6.71 |
|---|---|
| Polyglyceryl-2 caprate | 1.83 |
| Caprylic/capric triglycerides | 68.16 |
| Water | 17.20 |
| Propylene glycol | 6.1 |

W/O Microemulsions With Thickeners, Gels

EXAMPLE 30

| PEG-20 sorbitan monolaurate | 2.15 |
|---|---|
| Polyglycerol triisostearate (Polydermanol GE 40 DS) | 5.38 |
| Isopropyl myristate | 56.97 |
| Water | 28 |
| PI-50,000 (PEG-10,000)$_2$ | 7.5 |

EXAMPLE 31

| Polyglycerol diisostearate | 7.45 |
|---|---|
| Isopropyl myristate | 55.82 |
| Water | 28.73 |
| PI-50,000 (PEG-10,000)$_2$ | 8 |

EXAMPLE 32

| Steareth-2 | 5.66 |
|---|---|
| Steareth-16 | 2.77 |
| Cetearyl isononanoate | 65.29 |
| Water | 19.28 |
| PI-50,000 (PEG-10,000)$_2$ | 7 |

EXAMPLE 33

| PEG-20 octyl dodecyl ether | 4.12 |
|---|---|
| Ethyl hexyl glycerol ether | 4.12 |
| DicaprylyL ether | 63.28 |
| Water | 21.18 |
| PI-50,000 (PEG-10,000)$_2$ | 7.3 |

EXAMPLE 34

| Sorbitan laurate | 3.53 |
|---|---|
| PEG-20 sorbitan trioleate | 4.71 |
| Dicaprylyl ether | 63.58 |
| Water | 21.18 |
| PI-50,000 (PEG-10,000)$_2$ | 7 |

EXAMPLE 35

| Glyceryl isostearate | 3.0 |
|---|---|
| PEG-12 distearate | 4.0 |
| Dicaprylyl ether | 53.0 |
| Water | 33.0 |
| PI-50,000 (PEG-10,000)$_2$ | 7 |

EXAMPLE 36

| Lecithin | 6.71 |
|---|---|
| Polyglycerol-2 caprate | 1.83 |
| Caprylic/capric triglyceride | 61.16 |
| Water | 17.20 |
| PI-50,000 (PEG-10,000)$_2$ | 7 |
| Propylene glycol | 6.1 |

What is claimed is:

1. A water-in-oil microemulsion in the form of a gel, which comprises of:
   (a) an oily phase, which is essentially composed of constituents of low volatility, and
   (b) a discontinuous aqueous phase comprising:
      one or more polyethoxylated water-in-oil emulsifiers; and/or
      one or more polypropoxylated water-in-oil emulsifiers; and/or
      one or more polyethoxylated and polypropoxylated water-in-oil emulsifiers; and/or
      one or more monoesters, diesters, polyesters of polyols as water-in-oil emulsifiers; and/or
      one or more monoethers, diesters, polyesters of polyols as water-in-oil emulsifiers; and/or
      one or more dimethicone copolyols as water-in-oil emulsifiers; and/or
      one or more fatty alcohols or fatty acids and water-in-oil emulsifiers; and/or
      one or more sorbitan esters as water-in-oil emulsifiers; and/or
      one or more methylglucose esters as water-in-oil emulsifiers;
   (c) optionally furthermore comprising one or more oil-in-water emulsifiers wherein the total emulsifier content of said microemulsion gel is less than 20% by weight, based on the total weight of the emulsion; and wherein said microemulsion gels are prepared by mixing the aqueous phase, oily phase and one or more emulsifiers, wherein the HLB value of the emulsifier or mixture of emulsifiers being in the range of 2–14; and wherein the droplets of the discontinuous aqueous phase are joined to one another by one or more crosslinlking substances, wherein the crosslinking substances have:
   (i) at least one hydrophobic region which has an extension capable of bridging the distance between the droplets of the discontinuous aqueous phase; and (ii) at least one hydrophilic region which is capable of entering into a hydrophilic interaction with the droplets of the discontinuous aqueous phase.

2. A water-in-oil microemulsion in the form of a gel, which comprises of:

(a) a continuous oily phase, and
(b) a discontinuous aqueous phase comprising at least:
   one or more polyethoxylated water-in-oil emulsifiers; and/or
   one or more polypropoxylated water-in-oil emulsifiers; and/or
   one or more polyethoxylated and polypropoxylated water-in-oil emulsifiers; and/or
   one or more monoesters, diesters, polyesters of polyols as water-in-oil emulsifiers; and/or
   one or more monoethers, diesters, polyesters of polyols as water-in-oil emulsifiers; and/or
   one or more sorbitan esters as water-in-oil emulsifiers; and/or
   one or more silicone emulsifiers as water-in-oil emulsifiers; and/or
   one or more fatty alcohols or fatty acids and water-in-oil emulsifiers;
   wherein the water-in-oil emulsifiers are selected from the group consisting of:
   (b1) fatty alcohol ethoxylates of the formula R—O—($CH_2$—$CH_2$—O)$_n$—H, where R is branched or unbranched alkyl, aryl or alkenyl radical, and n is a number from 1 to 10;
   (b2) polyethylene glycol ethers of the formula R—O—($CH_2$—$CH_2$—O)$_n$—R', where R and R' independently of one another are branched or unbranched alkyl, aryl or alkenyl radical, and n is a number from 1 to 30,
   (b3) fatty acid ethoxylates of the formula R—COO—($CH_2$—$CH_2$—O)$_n$—H, where R is branched or unbranched alkyl or alkenyl radical, and n is a number from 1 to 20;
   (b4) esterified fatty acid ethoxylates of the formula R—COO—($CH_2$—$CH_2$—O)$_n$—C(O)—R', where R and R' independently of one another are branched or unbranched alkyl or alkenyl radicals, and n is a number from 1 to 20;
   (b5) esterified fatty acid ethoxylates of the formula R—COO—($CH_2$—$CH_2$—O)$_n$—C(O)—R', where R and R' independently of one another are branched or unbranched alky, hydroxyalkyl, or alkenyl radicals, and n is a number from 1 to 40;
   (b6) etherified fatty acid ethoxylates of the formula R—COO—($CH_2$—$CH_2$—O)$_n$—R', where R and R' independently of one another are branched or unbranched alkyl or alkenyl radicals, and n is a number from 1 to 30;
   (b7) fatty alcohol propoxylates of the formula R—O—($CH_2$—CH($CH_3$)—O)$_n$—H, where R is a branched or unbranched alkyl or alkenyl radical, and n is a number from 1 to 30;
   (b8) polyoxyethylene sorbitan fatty acid esters based on a branched or unbranched alkanoic or alkenoic acids and having a degree of ethoxylation between 1 to 10;
   (b9) cholesterol ethoxylates having a degree of ethoxylation between 1 to 10;
   (b10) ethoxylated glycerides having a degree of ethoxylation between 1 to 30;
   (b11) ethoxylated triglycerides having a degree of ethoxylation between 1 to 30;
   (b12) monoglycerol ethers of the type R—O—$CH_2$—CH(OH)—$CH_2$OH, where R is a branched or unbranched alkyl, aryl or alkenyl radical;
   (b13) monoglycerol esters of the type RC(O)O$CH_2$—CH(OH)—$CH_2$OH, where R is a branched or unbranched alkyl, hydroxyalkyl, aryl or alkenyl radical;
   (b14) diglycerol esters of the type RC(O)OC$H_2$—CH(OH)—$CH_2$OC(O)R', where R and R' independently of one another are branched or unbranched alkyl, hydroxyalkyl, aryl or alkenyl radicals, and n is a number from 1 to 30;
   (b15) polyglycerol mono-, di- or poly-esters, wherein the fatty acids are independently of one another are branched or unbranched alkyl, hydroxyalkyl or alkenyl radicals;
   (b16) pentaerythrital esters, where the fatty acid independently of one another are branched or unbranched alkyl, hydroxyalkyl or alkenyl radicals,
   (b17) propylene glycol esters, where the fatty acids independently of one another are branched or unbranched alkyl, hydroxyalkyl or alkenyl radicals;
   (b18) sorbitan esters, where the fatty acids independently of one another are branched or unbranched alkyl, hydroxyalkyl or alkenyl radicals;
   (b19) fatty alcohols R—OH and fatty acids RCOOH, where R is a branched or unbranched alkyl or alkenyl radical;
   (b20) silicone emulsifiers; and
   (b21) methylglucose esters, where the fatty acids independently of one another are branched or unbranched alkyl, hydroxyalkyl or alkenyl radicals;

(c) optionally furthermore comprising one or more oil-in-water emulsifiers;

wherein the total emulsifier content of said microemulsion gel is less than 20% by weight, based on the total weight of the emulsion; and wherein said microemulsion gels are prepared by mixing the aqueous phase, oily phase and one or more emulsifiers, wherein the HLB value of the emulsifier or mixture of emulsifiers being in the range of 2–14; and wherein the droplets of the discontinuous aqueous phase are joined to one another by one or more crosslinking substances, wherein the crosslinking substances are present in a range from 0.3–30% by weight, based on the total weight of the emulsion, and have:

(i) at least one hydrophobic region which has an extension capable of bridging the distance between the droplets of the discontinuous aqueous phase; and (ii) at least one hydrophilic region which is capable of entering into a hydrophilic interaction with the droplets of the discontinuous aqueous phase.

3. The microemulsion gels of claim 1, wherein the total amount of emulsifiers is less than 20% by weight, based on the total weight of the microemulsion gels.

4. The microemulsion gels of claim 3, wherein the total amount of emulsifiers is between 0.1–10% by weight, based on the total weight of the microemulsion gels.

5. The microemulsion gels of claim 1, wherein the total amount of crosslinking substances is from 0.3–30% by weight, based on the total weight of the microemulsion gels.

6. The microemulsion gels of claim 5, wherein the total amount of crosslinking substances is from 1–10% by weight, based on the total weight of the microemulsion gels.

7. The microemulsion gels of claim 1, wherein the total amount of emulsifiers is between 0.1–10% by weight, based on the total weight of the emulsion, and the total amount of crosslinking substances is from 1–10% by weight, based on the total weight of the emulsion.

8. The microemulsion gels of claim 7, wherein the one or more crosslinking substances are selected from the group consisting of hydrophilically substituted polyisoprenes, substituted PEG, substituted glyceryl and dimethicone copolyols.

9. The microemulsion gels of claim 7, wherein the hydrophilically substituted polyisoprenes are selected from the group consisting of PI-39,000 $(PEG-10,000)_2$, PI-50,000 $(PEG-5000)_2$, PI-50,000 $(PEG\ 10,000)_2$, PI-50,000 $(PEG\ 20,000)_2$, $PI(SO_3Li)_2$ and $PI(CO_2Na)_2$.

10. The microemulsion gels of claim 7, wherein the dimethicone copolyols have the formula $R-Si-(CH_3)_2O-(Si(CH_3)_2O)_n-Si(CH_3)_2R'$, where R and R' are independently branched or unbranched, saturated or unsaturated, cyclic or aliphatic, aromatic or heteroaromatic hydrophobic groups to which hydrophilic groups are covalently bonded and n is selected such that the dimethicone copolyol is soluble/dispersible in fat.

11. The microemulsion gels of claim 10, wherein R and R' are independently selected from the group consisting of:

$$-(CH_2)_y-(O-CH_2-CH(OH)-CH_2)_x OH; \text{ and} \qquad (a)$$

$$-(CH_2)_y-(OC_2H_4)_x-OH; \qquad (b)$$

wherein, $y=0-10^6$;

$x=1$ to $10^7$.

12. The microemulsion gels of claim 11, wherein n=30 to $10^7$, y=1 to 30 and x=2 to $10^6$.

13. The microemulsion gels of claim 12, wherein n=30 to $10^7$, y=2 to 20 and x=3 to 500.

14. The microemulsion gel of claim 9, wherein R and R' are $-CH_2CH_2CH_2(OCH_2CH_2)_{12}OH$ and n=148.

* * * * *